US009161728B2

(12) United States Patent
Watanabe et al.

(10) Patent No.: US 9,161,728 B2
(45) Date of Patent: Oct. 20, 2015

(54) X-RAY DIAGNOSIS APPARATUS AND X-RAY DIAGNOSIS ASSISTING METHOD

(71) Applicants: Kabushiki Kaisha Toshiba, Minato-ku (JP); Toshiba Medical Systems Corporation, Otawara-shi (JP)

(72) Inventors: Yuichiro Watanabe, Yaita (JP); Teruomi Gunji, Otawara (JP); Manabu Tanaka, Otawara (JP)

(73) Assignees: Kabushiki Kaisha Toshiba, Minato-ku (JP); Toshiba Medical Systems Corporation, Otawara-shi (JP)

( * ) Notice: Subject to any disclaimer, the term of this patent is extended or adjusted under 35 U.S.C. 154(b) by 175 days.

(21) Appl. No.: 13/954,303

(22) Filed: Jul. 30, 2013

(65) Prior Publication Data

US 2013/0315370 A1    Nov. 28, 2013

Related U.S. Application Data

(63) Continuation of application No. PCT/JP2013/002814, filed on Apr. 25, 2013.

(30) Foreign Application Priority Data

May 25, 2012 (JP) ................................. 2012-119830

(51) Int. Cl.
*A61B 6/10* (2006.01)
*A61B 6/12* (2006.01)
(Continued)

(52) U.S. Cl.
CPC ..... *A61B 6/10* (2013.01); *A61B 6/06* (2013.01); *A61B 6/12* (2013.01); *A61B 6/487* (2013.01); *A61B 6/542* (2013.01)

(58) Field of Classification Search
CPC .......... A61B 6/487; A61B 6/12; A61B 6/504; A61B 6/542
USPC ............................................. 378/42, 147–153
See application file for complete search history.

(56) References Cited

U.S. PATENT DOCUMENTS

| 7,539,284 B2 * | 5/2009 | Besson ........................... 378/62 |
| 2011/0013742 A1 * | 1/2011 | Zaiki et al. ..................... 378/15 |
| 2012/0189093 A1 | 7/2012 | Zaiki et al. |

FOREIGN PATENT DOCUMENTS

| CN | 101953691 A | 1/2011 |
| JP | 63-286170 | 11/1988 |

(Continued)

OTHER PUBLICATIONS

International Search Report issued on Jun. 18, 2013 for PCT/JP2013/002814 filed on Apr. 25, 2013 with English Translation of Categories.

(Continued)

*Primary Examiner* — Hoon Song
(74) *Attorney, Agent, or Firm* — Oblon, McClelland, Maier & Neustadt, L.L.P.

(57) ABSTRACT

An X-ray diagnosis apparatus of an embodiment includes: an imaging unit that includes an X-ray tube which emits an X-ray to a subject, and an X-ray detector which detects an X-ray passing through the subject; an X-ray beam limiting unit that is disposed between the X-ray tube and the X-ray detector, has a plurality of collimator blades, and can be rotated; an image processing unit that generates a fluoroscopic image of a region of interest set by the X-ray beam limiting unit; and a control unit that individually controls the plurality of collimator blades in such a way that a long side of an opening formed by the plurality of collimator blades goes in a longitudinal direction of a target within the fluoroscopic image.

10 Claims, 15 Drawing Sheets

(51) Int. Cl.
*A61B 6/06* (2006.01)
*A61B 6/00* (2006.01)

(56) References Cited

FOREIGN PATENT DOCUMENTS

| | | |
|---|---|---|
| JP | 2011-19633 | 2/2011 |
| JP | 2012-75782 | 4/2012 |

OTHER PUBLICATIONS

International Written Opinion issued on Jun. 18, 2013 for PCT/JP2013/002814 filed on Apr. 25, 2013.
Office Action issued Feb. 16, 2015 in Chinese Patent Application No. 201380000559.8 (with partial English translation).
Search Report issued Feb. 5, 2015 in Chinese Patent Application No. 201380000559.8 (with partial English translation).

* cited by examiner

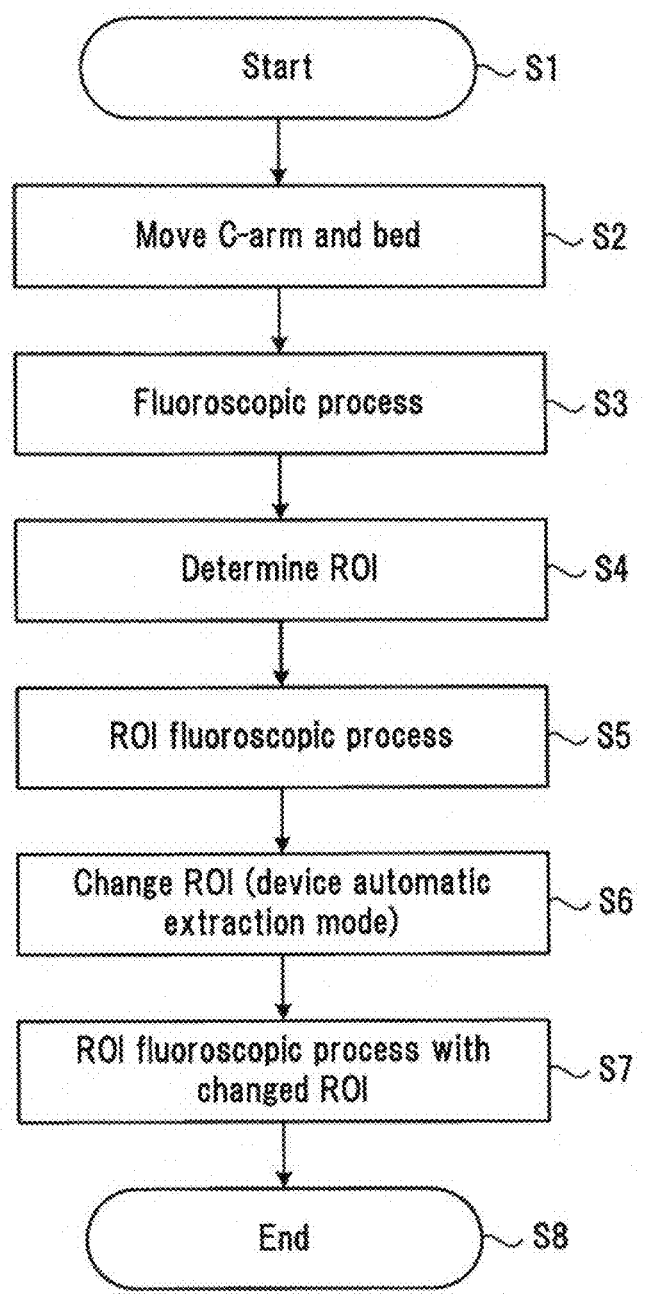

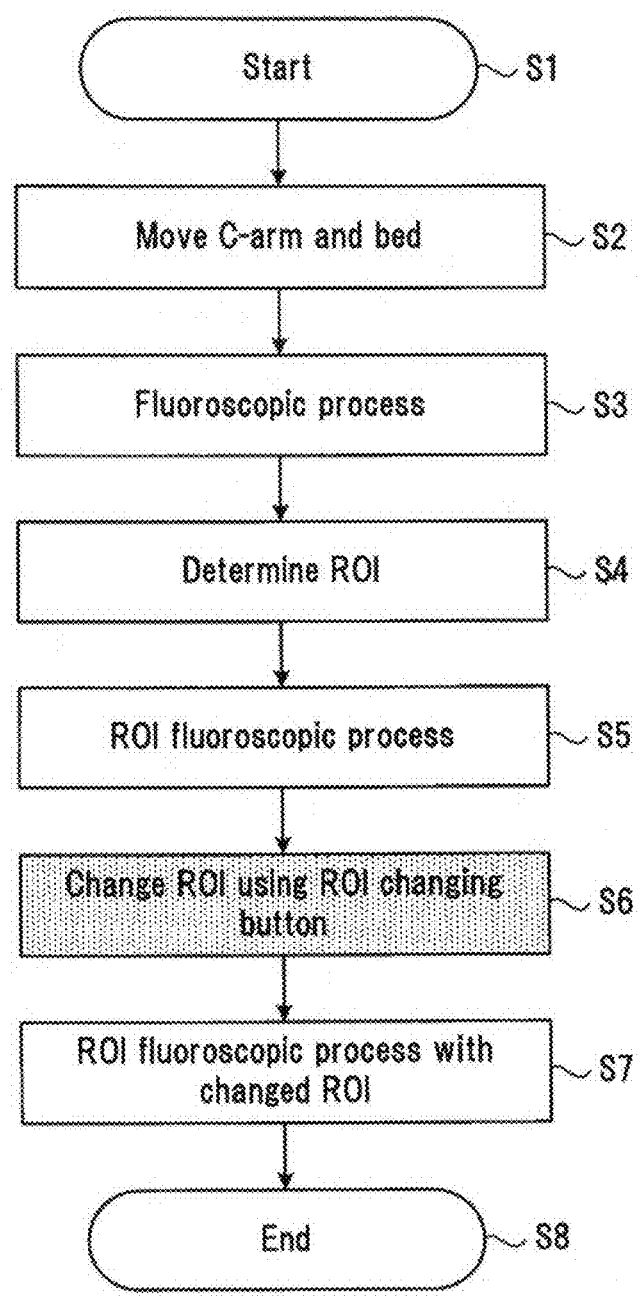

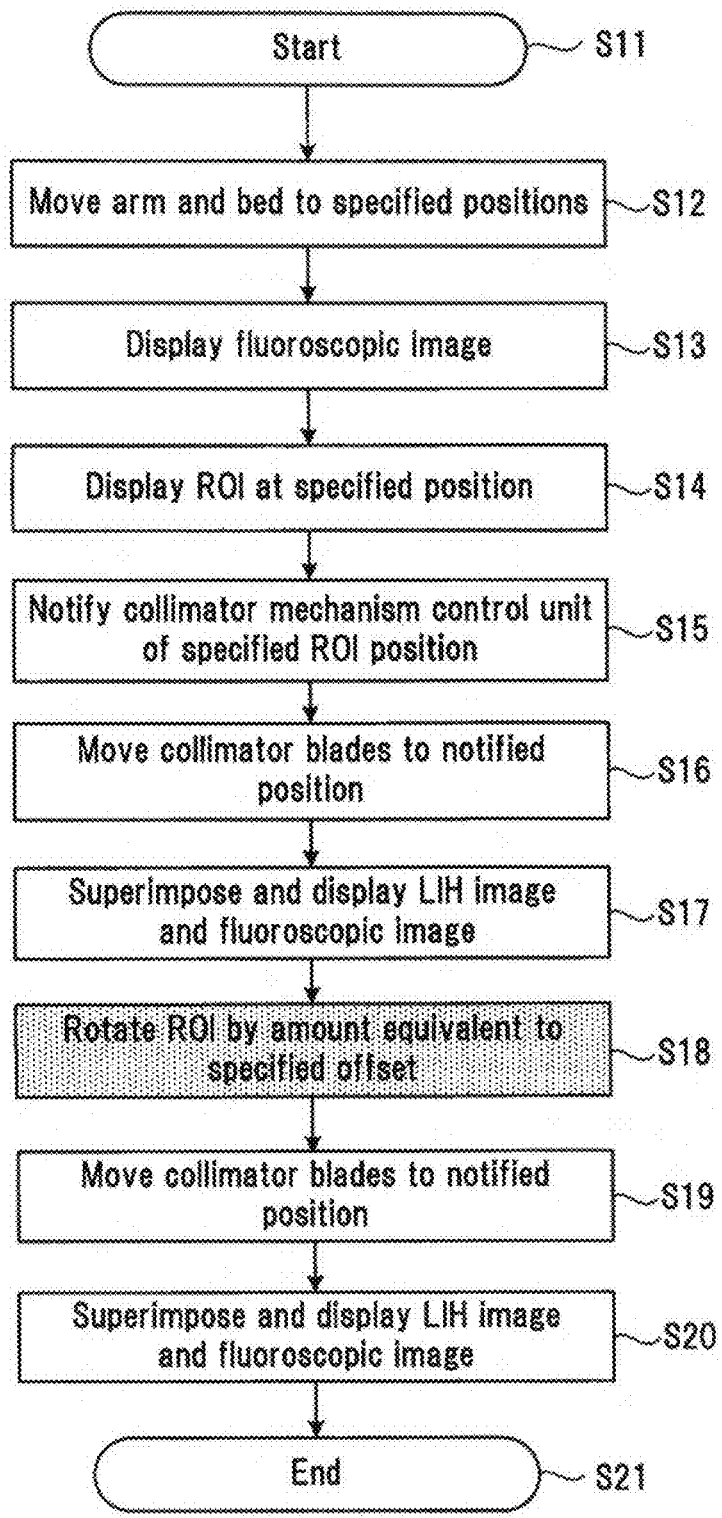

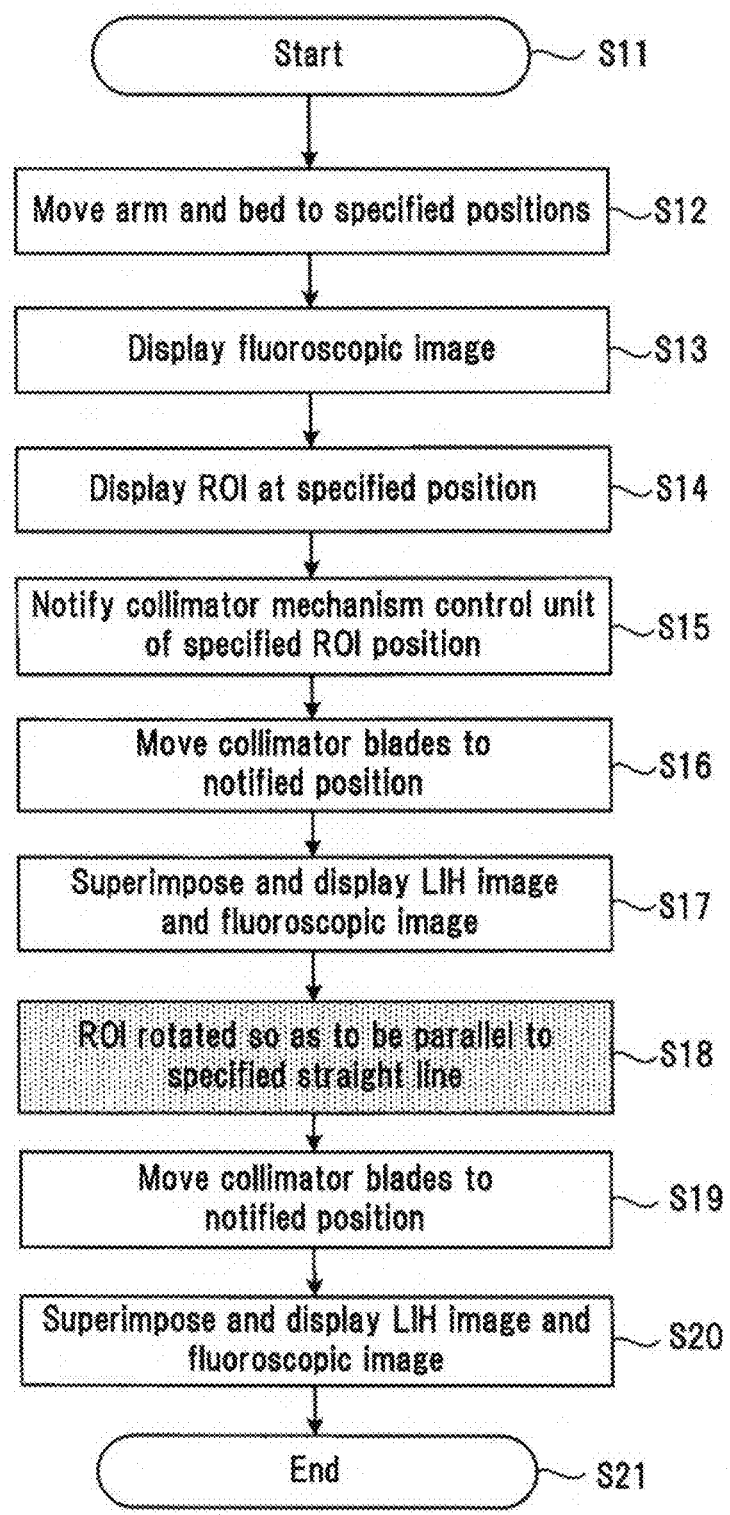

X-RAY DIAGNOSIS APPARATUS AND X-RAY DIAGNOSIS ASSISTING METHOD

CROSS-REFERENCE TO RELATED APPLICATION

This application is a continuation of International Application No. PCT/JP2013/002814, filed on Apr. 25, 2013, which is based upon and claims the benefit of priority from the prior Japanese Patent application No. 2012-119830, filed on May 25, 2012, the entire contents of which are incorporated herein by reference.

FIELD

Embodiments described herein relate to an X-ray diagnosis apparatus having an X-ray generation unit and an X-ray detector; and to an X-ray diagnosis apparatus that is designed to reduce an exposure dose by rotating and moving collimator blades of an X-ray beam limiting device in a way that narrows an irradiation field, and an X-ray diagnosis assisting method.

BACKGROUND

Conventionally, in endovascular treatment, angiographic examination, and the like, a catheter is inserted into a blood vessel, for example, from the base of a foot, and is brought to a target site via the blood vessel. When the catheter (or a guide wire that guides the catheter) is brought to the target site, an X-ray fluoroscopic image is displayed. Watching the displayed image, a user moves the catheter or the guide wire to an affected site.

In an X-ray diagnosis apparatus, an X-ray tube and an X-ray detector (which is generally a planar detector called FPD) are so disposed as to face each other, and, on a front of the X-ray tube, an X-ray beam limiting device is provided. The X-ray beam limiting device includes collimator blades that can slide. As the collimator blades are moved, a diagnosis area of a subject is selectively irradiated with X-rays. In this manner, the X-ray diagnosis apparatus is designed to protect the subject from unnecessary X-ray exposure.

However, the X-ray beam limiting device can move only in a horizontal direction (X-direction) and a vertical direction (Y-direction) with respect to FPD. If a blood vessel region that a user wants to see extends diagonally with respect to FPD (e.g., a blood vessel at the base of a foot), the problem arises that the irradiation field becomes larger, causing unnecessary exposure.

BRIEF DESCRIPTION OF THE DRAWINGS

FIG. 7 is a workflow diagram showing a ROI changing process of one embodiment from user's point of view;

FIG. 10 is a workflow diagram showing a ROI changing process of the second embodiment from user's point of view;

FIG. 11 is a workflow diagram showing a ROI changing process of the second embodiment from system's point of view;

FIG. 15 is a workflow diagram showing a ROI changing process of the third embodiment from system's point of view.

DETAILED DESCRIPTION

An X-ray diagnosis apparatus of an embodiment includes: an imaging unit that includes an X-ray tube which emits an X-ray to a subject, and an X-ray detector which detects an X-ray passing through the subject; an X-ray beam limiting unit that is disposed between the X-ray tube and the X-ray detector has a plurality of collimator blades, and can be rotated; an image processing unit that generates a fluoroscopic image of a region of interest set by the X-ray beam limiting unit; and a control unit that individually controls the plurality of collimator blades in such a way that a long side of an opening formed by the plurality of collimator blades goes in a longitudinal direction of a target within the fluoroscopic image.

Hereinafter, an X-ray diagnosis apparatus of one embodiment will be described in detail with reference to the accompanying drawings. Incidentally, the same portions in each diagram are represented by the same reference symbols.

First Embodiment

Figure 1:
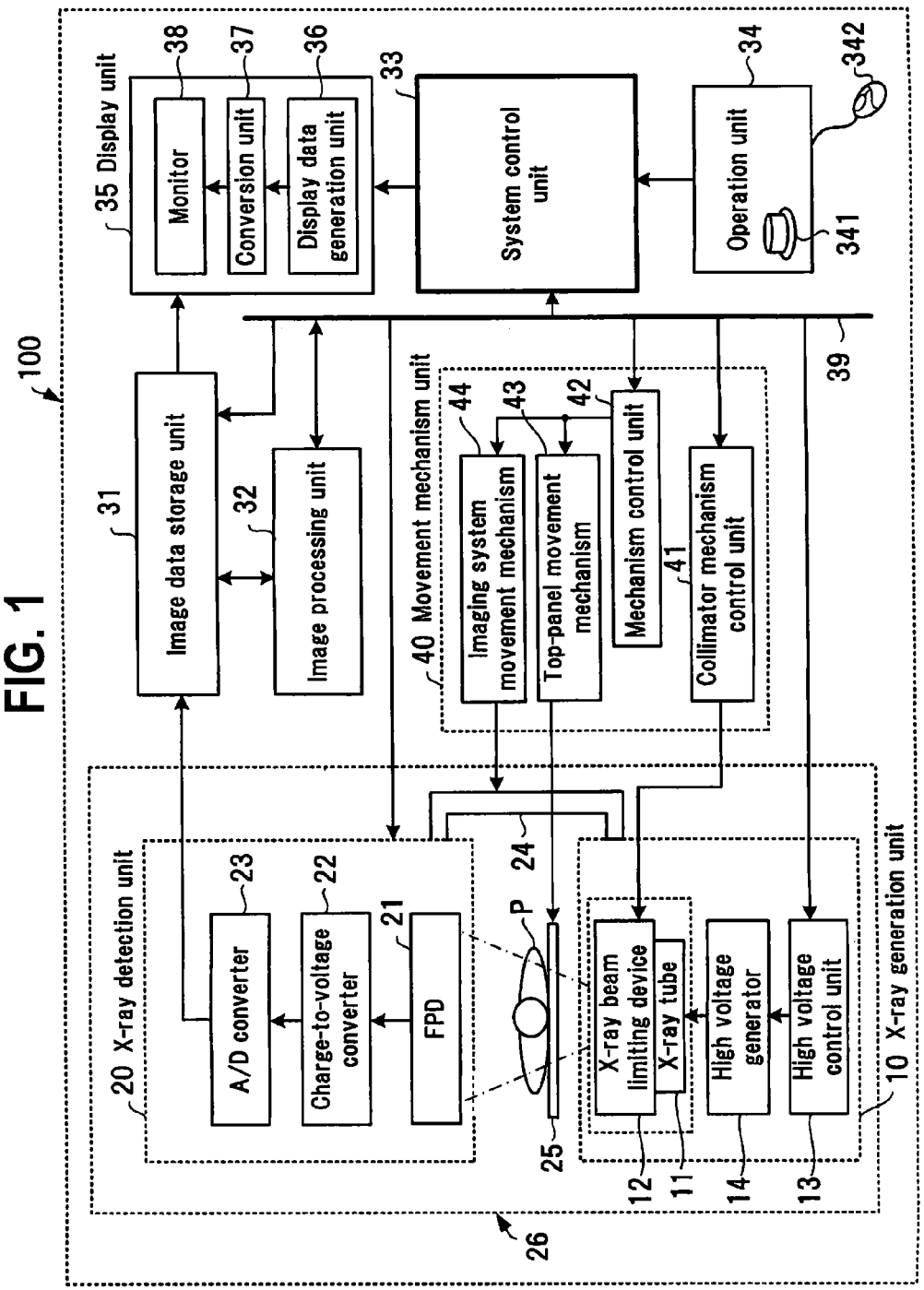
FIG. 1 is a block diagram showing the configuration of an X-ray diagnosis apparatus according to one embodiment.

FIG. 1 is a block diagram showing the configuration of an X-ray diagnosis apparatus according to one embodiment. FIG. 1 shows an X-ray diagnosis apparatus 100 called an angiography apparatus. The X-ray diagnosis apparatus 100 includes an X-ray generation unit 10, which generates an X-ray for a subject P, and an X-ray detection unit 20. The X-ray detection unit 20 detects an X-ray that has passed through the subject P in a two-dimensional manner, and generates X-ray projection data on the basis of the detection result.

The X-ray generation unit 10 includes an X-ray irradiation unit, which has an X-ray tube 11 and an X-ray beam limiting device 12 (X-ray beam limiting unit), and a high voltage control unit 13, and a high voltage generator 14. The X-ray tube 11 is a vacuum tube that generates an X-ray. The X-ray tube 11 is designed to accelerate electrons, which are emitted from a cathode (filament), using a high voltage to get the electrons colliding with a tungsten anode, thereby generating an X-ray. The high voltage control unit 13 controls the high voltage generator 14 in accordance with a command signal from a system control unit 33 (described later). That is, the system control unit 33 controls X-ray irradiation conditions, including a tube current and tube voltage of the X-ray tube 11, an X-ray pulse width, an irradiation period, an imaging section, and an irradiation time.

The X-ray detection unit 20 includes a FPD 21 (Flat Panel Detector); a charge-to-voltage converter 22 which converts electric charge read from the FPD 21 to voltage; and an A/D converter 23 which converts an output of the charge-to-voltage converter 22 to a digital signal. From the A/D converter 23, X-ray projection data is output. The FPD 21 constitutes an X-ray detector. The X-ray generation unit 10 and the X-ray detection unit 20 are supported by an arm (C-arm) 24. The C-arm 24 is able to move in a body-axis direction of the subject P placed on a top panel 25 of a bed. The C-arm 24 is also able to rotate around the body axis of the subject P. Incidentally, the X-ray generation unit 10 and the X-ray detection unit 20 constitute an imaging unit 26. As the C-arm 24 is rotated, the imaging unit 26 rotates around the subject P, imaging of the subject P from different angular directions.

The X-ray diagnosis apparatus 100 includes an image data storage unit 31, an image processing unit 32, the system control unit 33, an operation unit 34, and a display unit 35. In the image data storage unit 31, X-ray projection data from the A/D converter 23 is sequentially stored, and image data is generated. The image processing unit 32 performs imaging processing and calculation on the generated image data when needed in order to achieve objectives such as edge enhancement and improved S/N. Results of the image processing and calculation are stored in the image data storage unit 31. The image data stored in the image data storage unit 31 is read when necessary, and is supplied to the display unit 35 where the image data is displayed.

The system control unit 33 includes a CPU and a storage circuit (not shown), and runs on the basis of input information, setting information, and selection information from the operation unit 34. The system control unit 33 constitutes a control unit that takes overall control of each unit of the X-ray diagnosis apparatus 100 via a bus line 39.

The operation unit 34 allows users, such as a doctor or examiner, to input various commands and perform other operations. The operation unit 34 includes input devices, such as an operation button 341, a mouse 342, a switch, a keyboard, a trackball, and a joystick; an interactive interface equipped with a display panel, various switches, or the like. The operation unit 34 enables setting of a movement direction and movement speed of the top panel 25; a rotation/movement direction and rotation/movement speed of the imaging unit; and X-ray irradiation conditions, including the tube voltage and the tube current.

In order to display image data, the display unit 35 includes a display data generation unit 36, a conversion unit 37, and a monitor 38. The display data generation unit 36 combines image data with supplementary information, or converts image data into a predetermined display format to generate display data. The conversion unit 37 performs D/A (Digital/Analog) conversion and television format conversion on the display data to generate video signals. The generated video signals are displayed on the monitor 38, which is a liquid crystal monitor or the like.

The X-ray diagnosis apparatus 100 also includes a movement mechanism unit 40. The movement mechanism unit 40 includes a collimator mechanism control unit 41 and a mechanism control unit 42. The collimator mechanism control unit 41 controls the movement of collimator blades and other parts of the X-ray beam limiting device 12, and controls rotation of the X-ray beam limiting device 12. The mechanism control unit 42 controls a movement mechanism 43 of the top panel 25 on which the subject P is placed. The mechanism control unit 42 also controls an imaging system movement mechanism 44 of the imaging unit 26, C-arm 24, and the like. The movement mechanism unit 40 operates in response to an operation of the operation unit 34, and controls movements of each part under the control of the system control unit 33.

Figure 2:
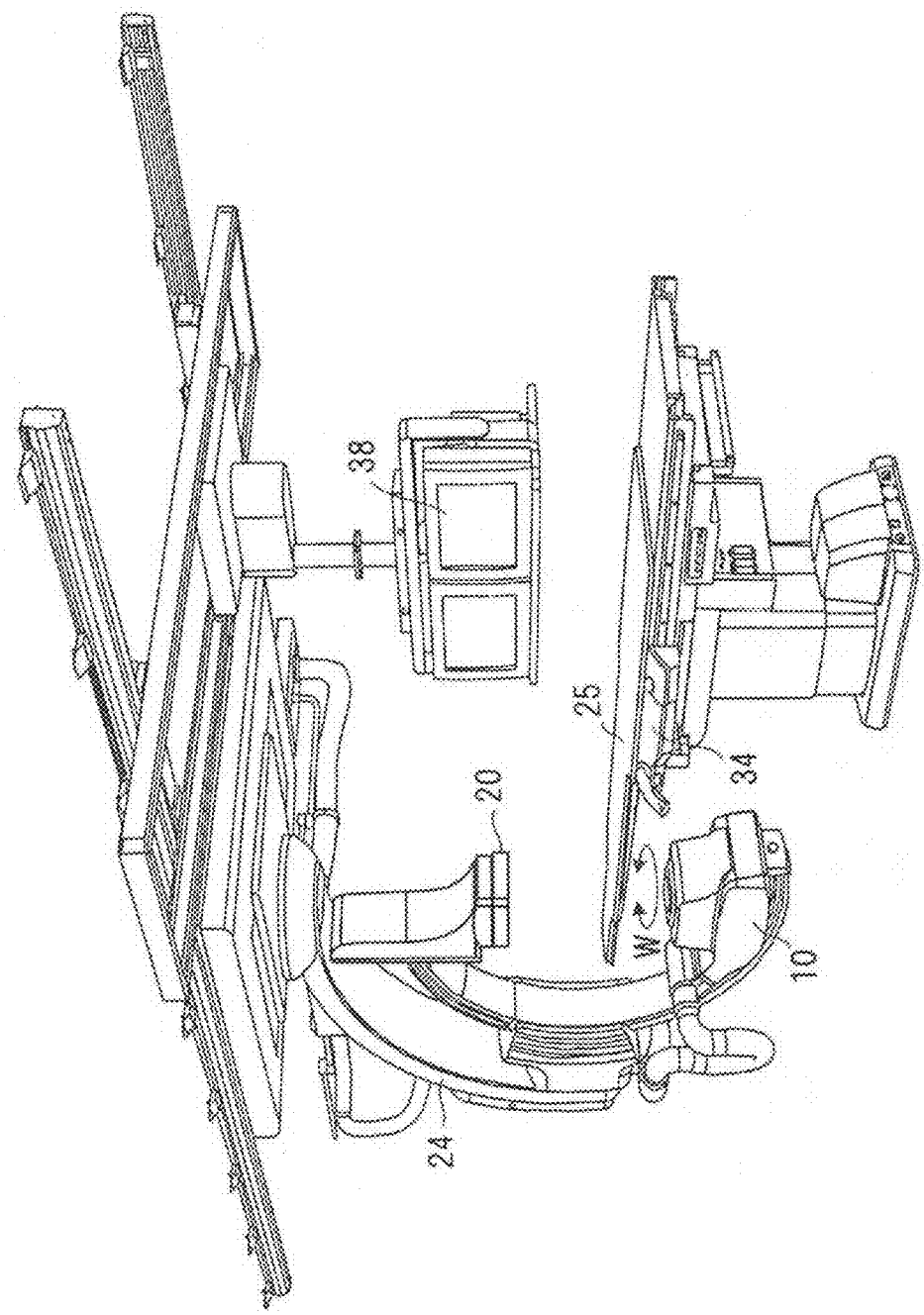
FIG. 2 is a perspective view showing the overall configuration of an X-ray diagnosis apparatus according to one embodiment.

FIG. 2 is a perspective view showing the overall configuration of the X-ray diagnosis apparatus 100 (angiography apparatus). In FIG. 2, the X-ray generation unit 10 and the X-ray detection unit 20 are supported by the C-arm 24 so as to face each other. A bed is disposed for the C-arm 24. On the top panel 25 of the bed, a subject (not shown) is placed. The position and height of the top panel 25 is controlled by the mechanism control unit 42. While the X-ray generation unit 10 faces the X-ray detection unit 20, the X-ray beam limiting device 12 is able to rotate as indicated by arrow W. The X-ray beam limiting device 12 can rotate independently of the FPD 21.

The C-arm 24 is supported by a rail provided on a ceiling section, for example. The C-arm 24 can move in a body-axis direction, from the head of the subject to the leg. As the C-arm 24 is rotated, the imaging unit 26 (the X-ray generation unit 10 and the X-ray detection unit 20) rotates around the body axis of the subject. The imaging unit 26 can slide and rotate along the C-arm 24.

X-ray projection data is processed by the image processing unit 32, and image data is displayed on the monitor 38. The monitor 38 is attached to the ceiling section, for example. To the bed, the operation unit 34 is attached. In response to an operation of the operation unit 34, the system control unit 33 controls the height of the top panel 25, and the movement and rotation of the C-arm 24; adjusts an irradiation range of an X-ray; controls an irradiation timing; and performs other operations.

Figure 3A:
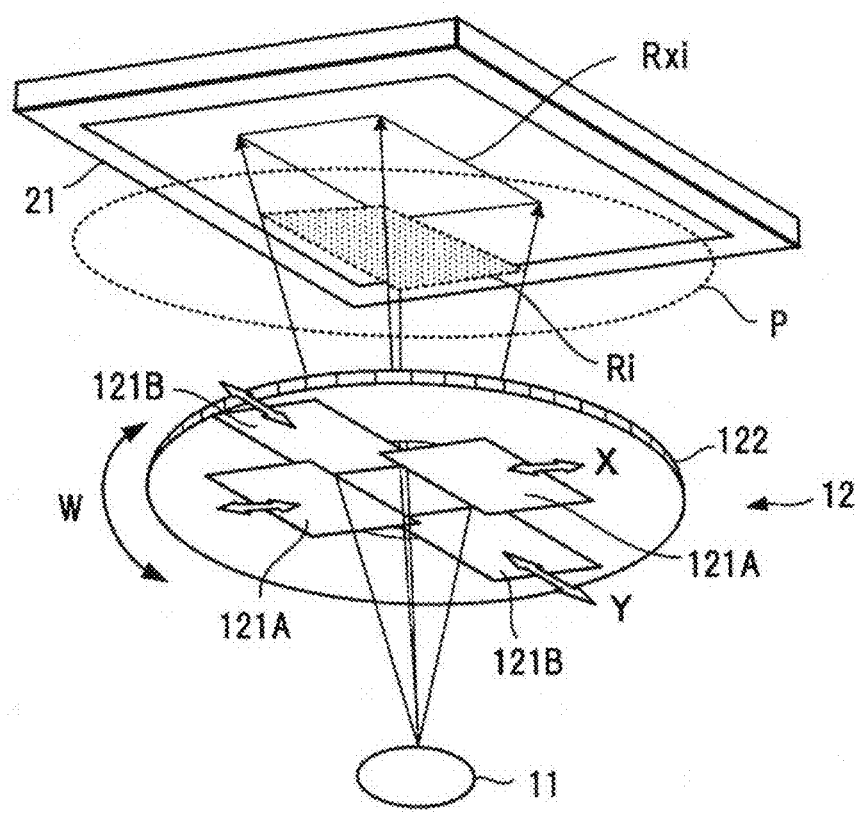
FIGS. 3A and 3B are schematic configuration diagrams of an X-ray beam limiting device according to one embodiment.

FIG. 3A is a schematic configuration diagram (perspective view) of the X-ray beam limiting device 12. As shown in FIG. 3A, the X-ray beam limiting device 12 is designed to regulate an X-ray irradiation region of the subject P. The X-ray beam limiting device 12 includes collimator blades 121A and 121B that enable a partial imaging region, which is set within an imageable region of the FPD 21, to be irradiated with a cone beam emitted from the X-ray tube 11. The collimator blades 121A and 121B can move in directions indicated by arrows X and Y as shown in FIG. 3A. The collimator blades 121A and 121B are moved by the collimator mechanism control unit 41. In this manner, the position and size of an opening is arbitrarily changed, and a region of interest is set.

As a result, an opening is formed by the collimator blades 121A and 121B. An imaging region RXi of the FPD 21 is formed by an X-ray that has passed through the opening and the region of interest Ri of the subject P. The FPD 21 converts the X-ray that has passed through the region of interest Ri of the subject P into electric charges, and accumulates the electric charges. By reading the accumulated electric charges, the FPD 21 generates X-ray projection data.

The collimator blades 121A and 121B are supported by a rotation unit 122. The collimator mechanism control unit 41 rotates the rotation unit 122 around an optical axis of the X-ray, thereby rotating an opening formed by the collimator blades 121A and 121B. In this manner, the angle of the imaging region RXi of the FPD 21 can be changed.

Figure 3B:
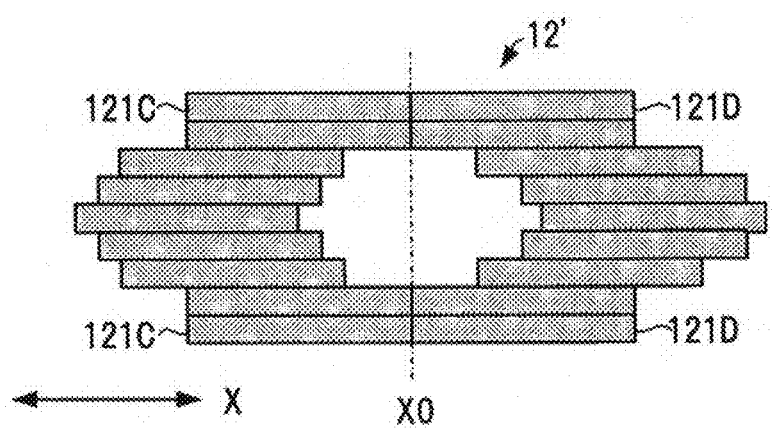

The X-ray beam limiting device 12 (X-ray beam limiting unit) is not limited to that in the example shown in FIG. 3A. For example, an X-ray beam limiting device 12' of a multi-leaf type may be used as shown in FIG. 3B. FIG. 3B is a schematic configuration diagram (plane view) of the X-ray beam limiting device 12' of a multi-leaf type. The X-ray beam limiting device 12' includes a plurality of leaves 121C and 121D, which can freely advance and retreat along an X-axis and are in a rectangular shape.

A plurality of leaves 121C and 121D constitute collimator blades. Two leaves 121C and 121D on both sides of a central axis X0 are paired. The two leaves 121C and 121D that are paired are moved along the X-axis to turn the opening (irradiation field) into any shape other than a rectangular shape. When the multi leaf-type X-ray beam limiting device 12' is supported on the rotation unit 122, the X-ray beam limiting device 12' can be rotated in the direction of 'W'. The X-ray beam limiting device 12 shown in FIG. 3A, and the multi leaf-type X-ray beam limiting device 12' shown in FIG. 3B may be used in combination.

The following describes how to control an X-ray beam limiting device of the embodiment, as well as an example of displaying a fluoroscopic image. Incidentally, what is described below is the case where the X-ray beam limiting device 12 shown in FIG. 3A is used.

For example, in endovascular treatment, angiographic examination, and the like, a device, such as a catheter or a guide wire that guides the catheter, is inserted into a blood vessel, and is brought to a target site via the blood vessel. When the device is brought to the target site, an X-ray fluoroscopic image is displayed. Watching the displayed image, a user moves the device to an affected site.

According to the embodiment, first, the subject P is placed on the top panel 25, and the C-arm 24 and the top panel 25 are moved to a specified position. The subject P is then irradiated with an X-ray, and a fluoroscopic image is displayed. The term "fluoroscopic" means a process of emitting an X-ray with a small radiation dose and providing moving pictures in real time, assisting a user in positioning of a patient or endovascular treatment. Watching the fluoroscopic image, a user determines a region of interest (ROI) to see therethrough. That is, the LIH (Last Image Hold) image that the user sees through is used as a background image. The fluoroscopic image (ROI fluoroscopic image), which is obtained as the irradiation field is narrowed by the collimator blades 121A and 121B of the X-ray beam limiting device 12, is superimposed on the LIH image to be displayed.

Figure 4:
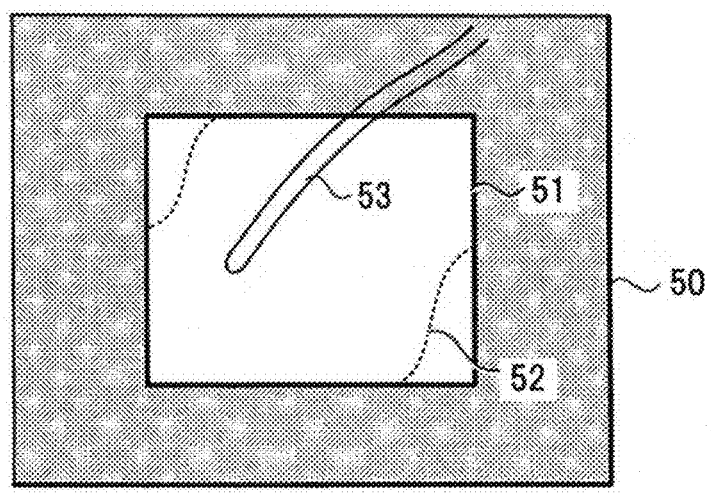
FIG. 4 is an explanatory diagram showing one example of an X-ray fluoroscopic image according to one embodiment.

FIG. 4 shows one example of an X-ray fluoroscopic image displayed on the monitor 38. In FIG. 4, on a display screen 50 of the monitor 38, an ROI fluoroscopic image 51 is displayed. On the ROI fluoroscopic image 51, a LIH image 52 is displayed as a background image. Because of the fluoroscopic image, a device image 53 is displayed.

The ROI is specified as a user (doctor or examiner) operates the operation section 34. Information about the specified ROI is transmitted to the collimator mechanism control unit 41 via the system control unit 33. The collimator mechanism control unit 41 controls the positions of the collimator blades 121A and 121B of the X-ray beam limiting device 12 to narrow the irradiation field. The above has described general settings of the ROI.

Figure 5A:
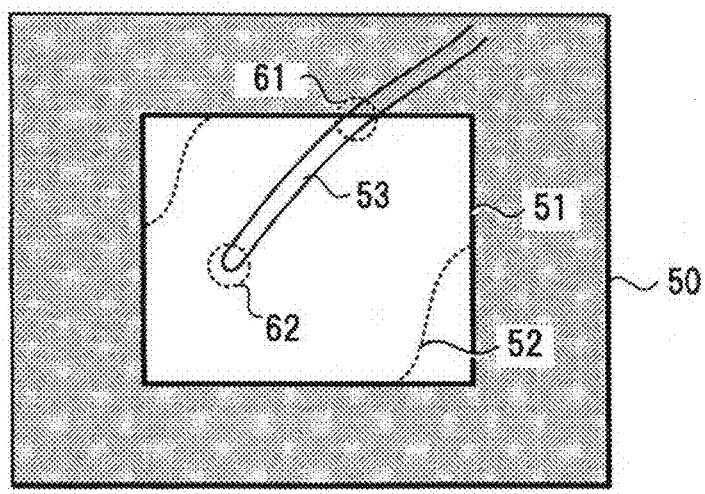
FIGS. 5A to 5C are explanatory diagrams showing a ROI changing process according to one embodiment.
Figure 5B:
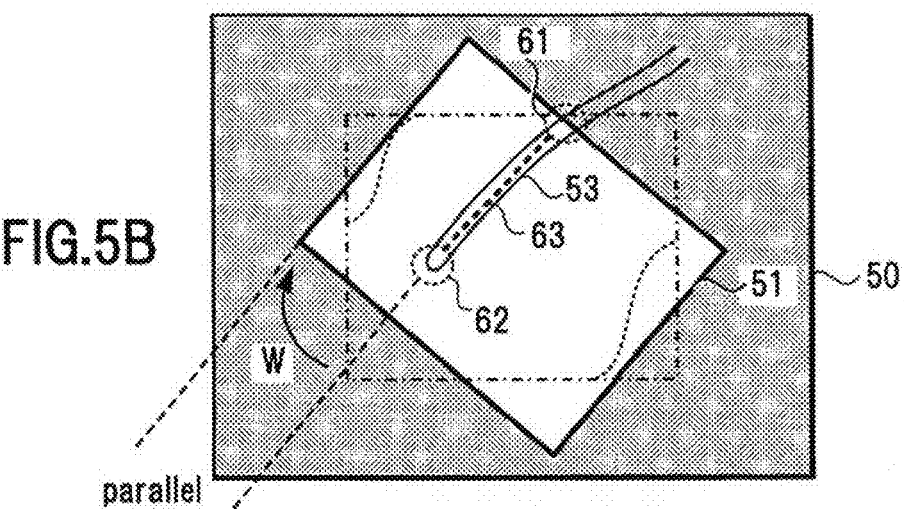
Figure 5C:
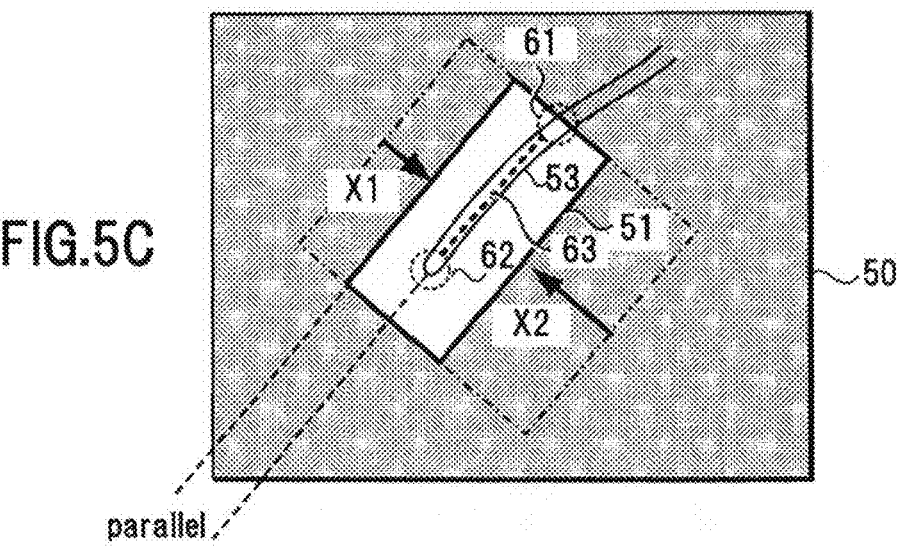

FIGS. 5A to 5C are diagrams illustrating a ROI changing process. As shown in FIG. 5A, on the fluoroscopic image (ROI fluoroscopic image) 51 which is obtained as the irradiation field is narrowed by the collimator blades 121A and 121B, the image 53 of a device which is a target, is displayed. The ROI is set around the position of the device.

If the device such as catheter, extends diagonally (due to a blood vessel at the base of a foot or the like, for example), the collimator blades 121A and 121B can move only in the X- and Y-directions even as the irradiation field is narrowed by the collimator blades 121A and 121B. Accordingly, in order to confirm the entire device that extends diagonally on the fluoroscopic image, the region of interest needs to become larger, causing unnecessary exposure for the subject P.

Therefore, according to the first embodiment, as shown in FIG. 5A, what is calculated is a straight line 63 connecting a start point 61 and endpoint 62 of the device image 53 in the ROI fluoroscopic image 51. The image processing unit 32 calculates the straight line 63. That is, the image processing unit 32 detects, based on image data of the ROI fluoroscopic image 51, the device image 53 to obtain coordinates of the start point 61 and endpoint 62 of the device image 53 in the ROI fluoroscopic image 51. Then, as shown in FIG. 5B, the image processing unit 32 calculates components of the line (straight line 63) connecting the start point 61 and the end point 62. The straight line 63 is a line that runs parallel to the longitudinal direction of the target (device image 53).

Then, the image processing unit 32 rotates the ROI (or a frame of the ROI image 51), so that one side of the ROI runs parallel to the calculated straight line 63. That is, one side of the ROI becomes parallel to the longitudinal direction of the device image 53. Information about the rotated ROI is transmitted to the collimator mechanism control unit 41. Incidentally, if one side of the ROI is parallel to the calculated straight line 63 in the first place, there is no need to rotate the ROI.

As shown in FIG. 5C, the collimator mechanism control unit 41 rotates the rotation unit 122 (FIG. 3A) of the X-ray beam limiting device 12 around the optical axis in the direction of 'W'. Moreover, in a direction perpendicular to the straight line 63 (device image 53), the positions of the collimator blades 121A and 121B are controlled in such a way as to move closer to the straight line 63. For example, the positions of the collimator blades 121A are moved in X1- and X2-directions to change the ROI.

As a result, the ROI becomes smaller, and the ROI fluoroscopic image 51, too becomes smaller in size, thereby reducing radiation exposure for the subject P. Even as the ROI becomes smaller, the device image 53 is displayed without any problem, assisting the progression of the device.

The collimator blades 121A and 121B are set in advance so as to approach a preset distance from the straight line 63. Therefore, the ROI can be automatically changed. Accordingly, even when the device image 53 extends diagonally, the X-ray beam limiting device 12 is rotated in accordance with the inclination angle of the device image 53, and the positions of the collimator blades 121A and 121B are controlled. In this manner, the ROI can be changed.

Incidentally, FIG. 5C shows an example in which the changed ROI is in a rectangular shape. However, if the multi leaf-type X-ray beam limiting device 12' shown in FIG. 3B is used, the ROI may be changed not only into a rectangular shape, but also into an elongated elliptical shape.

Figure 6A:
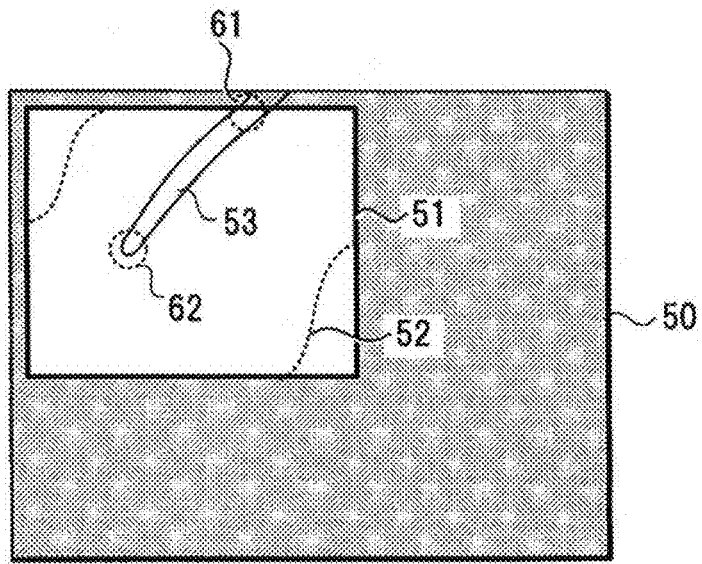
FIGS. 6A and 6B are explanatory diagrams showing other examples of displaying an X-ray fluoroscopic image according to one embodiment.
Figure 6B:
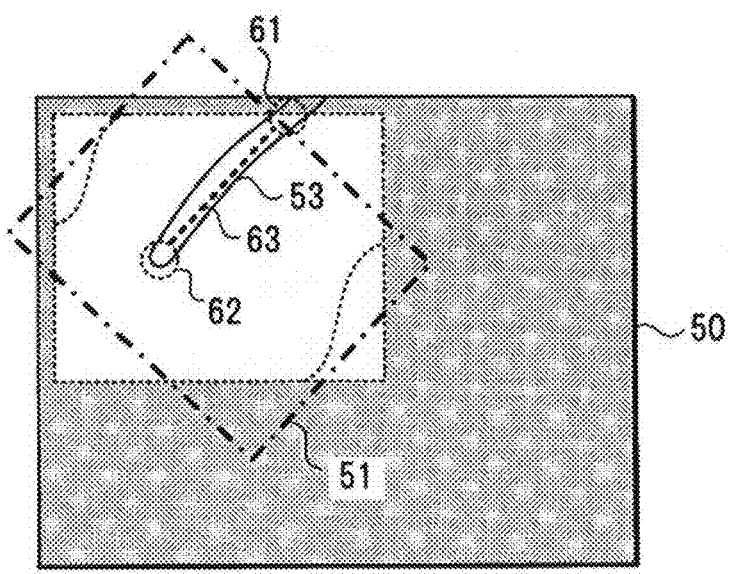

FIGS. 6A and 6B are diagrams showing the ROI fluoroscopic image 51 of the case where the ROI is away from the center of the FPD 21. As shown in FIG. 6A, when the ROI is away from the center of the FPD 21, the straight line 63 connecting the start point 61 and end point 62 of the device image 53 in the ROI fluoroscopic image 51 appears at a corner of the FPD 21. If the ROI is rotated, as shown in FIG. 6B, an X-ray is emitted to outside the FPD 21. Therefore, if a region outside the FPD 21 is irradiated with an X-ray as the ROI is rotated, the rotation is stopped.

FIG. 7 is a workflow diagram showing a ROI changing process from user' point of view. In FIG. 7, step S1 is a start step. At step S2, the subject P is placed on the top panel 25 of the bed, and the C-arm 24 and the top panel 25 are moved. At step S3, an X-ray is emitted to the subject P to carryout a fluoroscopic process. At the next step S4, the user determines the ROI while watching the fluoroscopic image.

At step S5, which follows a process of determining the ROI, a ROI fluoroscopic process is carried out. At step S6, the procedure described in FIGS. 5A to 5C is used to automatically extract the device image 53 and change the ROI. At step S7, the changed ROI is used to carry out a ROI fluoroscopic process. Checking the position of the device, the user moves the device forward. Step S8 is an end step.

Figure 8:
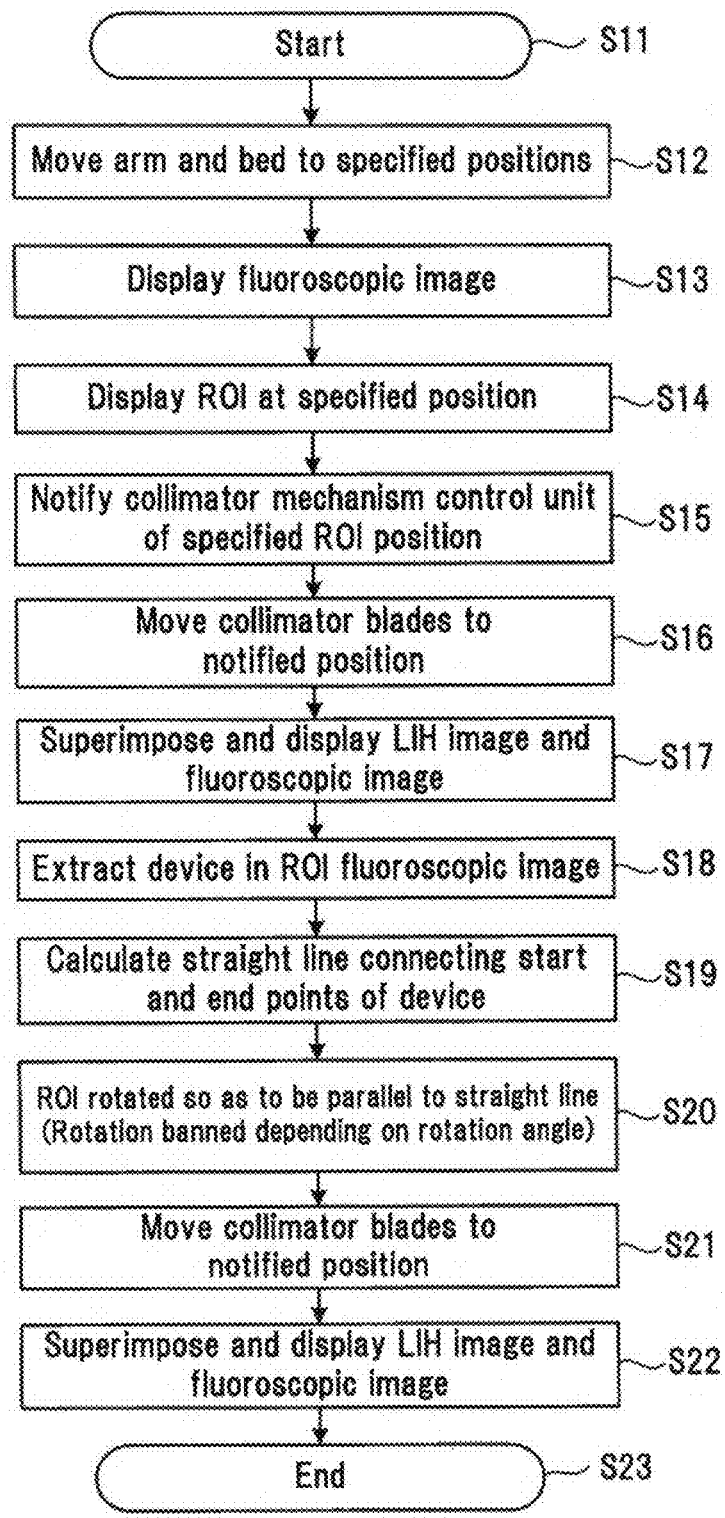
FIG. 8 is a workflow diagram showing a ROI changing process of one embodiment from system's point of view.

FIG. 8 is a workflow diagram showing a ROI changing process from system's point of view. In FIG. 8, step S11 is a start step. At step S12, the C-arm 24 and the top panel 25 are moved to specified locations. At step S13, an X-ray is emitted to the subject P to carry out a fluoroscopic process, and a fluoroscopic image is displayed on the monitor 38. At step S14, at a specified position of the display screen 50 of the monitor 38, the ROI is displayed. At step S15, the collimator mechanism control unit 41 is notified of the position of the specified ROI.

At step S16, the collimator mechanism control unit 41 moves the collimator blades 121A and 121B to the notified position. At step S17, the LIH image 52 and the ROI fluoroscopic image 51 are superimposed and displayed on the display screen 50 (see FIG. 5A). At the next step S18, the device image 53 in the ROI fluoroscopic image 51 is detected and extracted. At step S19, the straight line 63 connecting the start point 61 and end point 62 of the device image is calculated. At step S20, the ROI is so rotated that one side of the ROI becomes parallel to the straight line 63 (see FIG. 5B). However, if the rotation angle is such that an X-ray is emitted to outside the FPD 21 as described in FIG. 6, the rotation is banned. For example, a warning, such as the message "rotation is impossible," may be issued.

At step S21, as the ROI is rotated, the collimator mechanism control unit 41 is notified of new ROI information. The collimator mechanism control unit 41 moves the collimator blades 121A and 121B to the notified position. At step S22, the ROI fluoroscopic image 51, which is designed to see through with the changed ROI is superimposed on the LIH image 52, and is displayed (see FIG. 5C). Step S23 is an end step.

According to the above-described first embodiment, the device image within the ROI is automatically detected, and the ROI is so rotated as to be substantially parallel to the device image. Then, the ROI is so changed as to exist in a preset region around the device. Therefore, it is possible to reduce radiation exposure for the subject P.

Second Embodiment

Figure 9A:
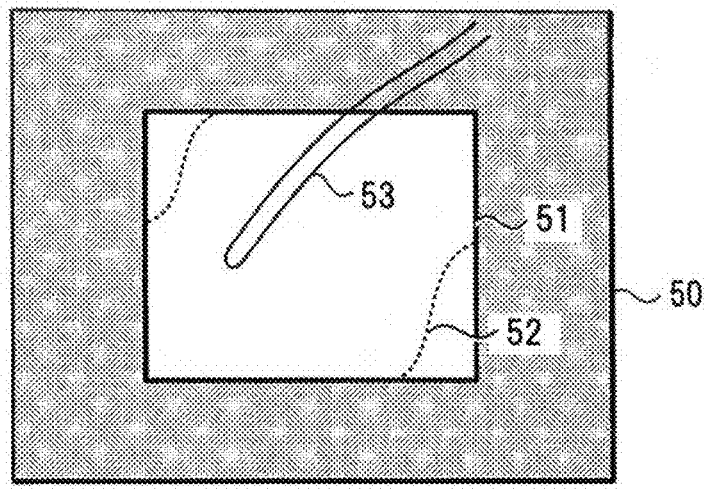
FIGS. 9A to 9C are explanatory diagrams showing a ROI changing process according to a second embodiment.
Figure 9B:
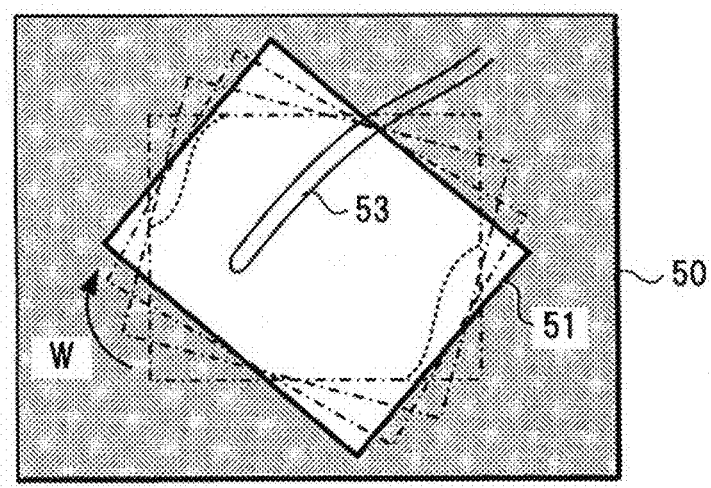
Figure 9C:
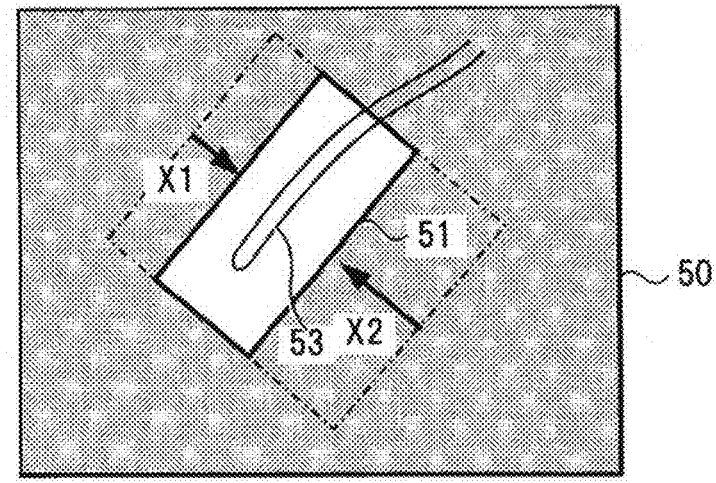

The following describes an X-ray diagnosis apparatus according to a second embodiment. According to the second embodiment, a user operates a button to order rotation of the X-ray beam limiting device 12. FIGS. 9A and 9C are diagrams illustrating a ROI changing process according to the second embodiment.

As shown in FIG. 9A, on the ROI fluoroscopic image 51, which is obtained as the irradiation field is narrowed by the collimator blades 121A and 121B, the image 53 of a device which is a target, is displayed. As shown in FIG. 9B, a user operates the operation unit 34 to rotate the ROI (or a frame of the ROI image 51). The image processing unit 32 transmits information about the rotated ROI to the collimator mechanism control unit 41 via the system control unit 33.

For example, in the operation unit 34, an operation button 341 is provided to enable a user to order the rotation of the ROI. Each time the user pushes the operation button 341, the ROI is rotated by an amount equivalent to a predetermined offset. The user rotates the ROI until one side of the ROI reaches an angle at which the side is substantially parallel to the device image 53. After the user pushes a decision key (not shown), the rotation is stopped. Incidentally, the operation button 341 which enables a user to order the rotation, may be a dial button, the ROI is rotated in accordance with the rotation direction and rotation angle of the dial button.

As shown in FIG. 9C, the collimator mechanism control unit 41 receives the information about the rotated ROI, and rotates the rotation unit 122 of the X-ray beam limiting device 12 in the direction of 'W'. In response to an operation by the user, the collimator mechanism control unit 41 controls the positions of the collimator blades 121A and 121B. The collimator mechanism control unit 41 brings the collimator blades 121A and 121B closer to the device image 53 in changing the ROI. For example, the collimator blades 121A are moved in the and X2-directions. As a result, the ROI fluoroscopic image 51 is changed in size, and the subject P's exposure to radiation is reduced.

Therefore, even when the device image 53 extends diagonally, the operation by the user makes it possible to rotate the X-ray beam limiting device 12 in accordance with the inclination angle of the device image 53, and control the positions of the collimator blades 121A and 121B to change the ROI.

Incidentally, as shown in FIG. 6A, if the ROI is away from the center of the FPD 21, and if an X-ray is emitted to outside the FPD 21 after the ROI is rotated, a warning message may be issued to urge a user to stop the rotation of the X-ray beam limiting device 12.

FIG. 10 is a workflow diagram showing a ROI changing process of the second embodiment from user's point of view. In the case of FIG. 10, steps S1 to S5 are the same as those of the first embodiment. However, step S6 is different.

That is, at step S6, the operation button 341 of the operation unit 34 is used to change the ROI. At step S7, the changed ROI is used to carry out a ROI fluoroscopic process. Moreover, at step S7, the user moves the device forward while checking the position of the device, and the process comes to an end at step S8.

FIG. 11 is a workflow diagram showing a ROI changing process of the second embodiment from system's point of view. In the case of FIG. 11, steps S11 to S17 are the same as those of the first embodiment. However, step S18 is different.

That is, at step S18, as the user operates the operation button 341, the ROI is rotated by an amount equivalent to a specified offset (see FIG. 9B). However, as described in FIG. 6B, if the rotation angle is such that an X-ray is emitted to outside the FPD 21, a message is issued to ban the rotation.

At the next step S19, as the ROI is rotated, the collimator mechanism control unit 41 is notified of new ROI information. The collimator mechanism control unit 41 moves the collimator blades 121A and 121B to the notified position (see FIG. 9C). At step S20, the ROI fluoroscopic image 51, which is designed to see through with the changed ROI, is superimposed on the LIH image 52, and is displayed. Step S21 is an end step.

Figure 12A:
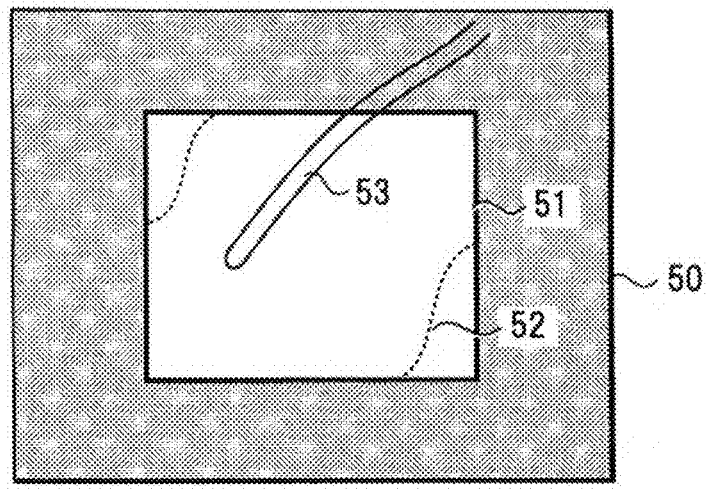
FIGS. 12A to 12C are explanatory diagrams showing a ROI changing process according to a modified example of the second embodiment.
Figure 12B:
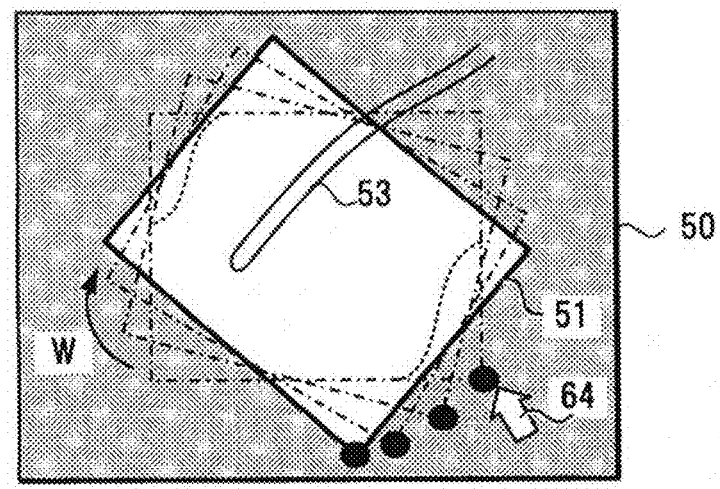
Figure 12C:
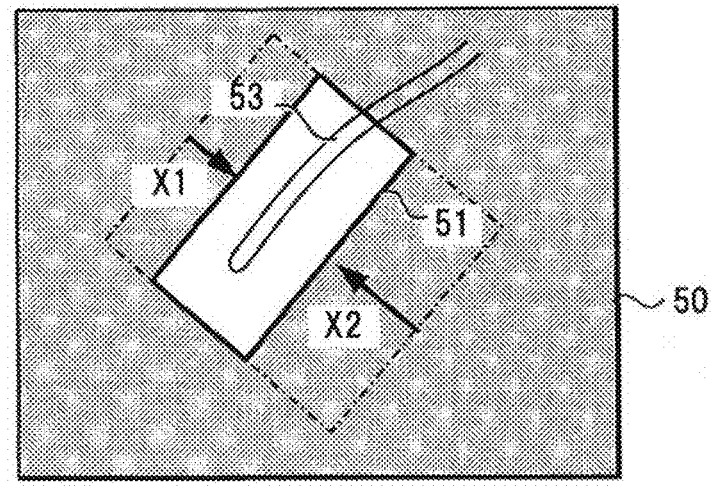

FIGS. 12A to 12C are diagrams illustrating a ROI changing process of an X-ray diagnosis apparatus according to a modified example of the second embodiment. In the case of FIG. 12, a user operates a mouse 342 provided in the operation unit 34 to order rotation of the X-ray beam limiting device 12.

As shown in FIG. 12A, on the ROI fluoroscopic image 51, which is obtained as the irradiation field is narrowed by the collimator blades 121A and 121B, the device image 53 is displayed. As shown in FIG. 12B, a user operates the mouse 342 to rotate the ROI. The image processing unit 32 transmits information about the rotated ROI to the collimator mechanism control unit 41 via the system control unit 33.

Operating the mouse 342, the user positions a cursor 64 at a corner of the ROI fluoroscopic image 51 to move in a rotation direction. By operating the mouse 342, the user can specify an angle by which the ROI is rotated, and a direction in which the ROI is rotated. The user rotates the ROI until one side of the ROI reaches a position where the side is substantially parallel to the device image 53.

Then, as shown in FIG. 12C, the collimator mechanism control unit 41 receives information about the rotated ROI, and rotates the rotation unit 122 of the X-ray beam limiting device 12 in the direction of 'W'. In response to an operation by the user, the collimator mechanism control unit 41 controls the positions of the collimator blades 121A and 121B. That is, the collimator blades 121A and 121B move in a direction that makes the collimator blades 121A and 121B closer to the device image 53, changing the ROI. As a result, the ROI fluoroscopic image 52 is decreased in size, and the subject P's exposure to radiation is reduced.

Incidentally, as shown in FIG. 6A, if the ROI is away from the center of the FPD 21, and if an X-ray is emitted to outside the FPD 21 after the ROI is rotated, a warning message may be issued to urge a user to stop the rotation of the X-ray beam limiting device 12.

In the example shown in FIGS. 12A to 12C, the same process as that shown in the workflow diagrams of FIG. 10 and FIG. 11 is performed. However, the process of step S6 of FIG. 10 is replaced with a process of "changing the ROI using the mouse." Moreover, the process of step S18 of FIG. 11 is replaced with a process of "rotating the ROI by an amount specified by the mouse."

As described above, according to the second embodiment, the user can rotate the ROI. The ROI can be so changed as to exist in a region around the device image. Therefore, it is possible to reduce radiation exposure for the subject P.

Third Embodiment

The following describes an X-ray diagnosis apparatus according to a third embodiment. According to the third embodiment, in response to an operation by a user, a parallel line is drawn near the device image 53. The drawn line is used to rotate the X-ray beam limiting device 12.

Figure 13A:
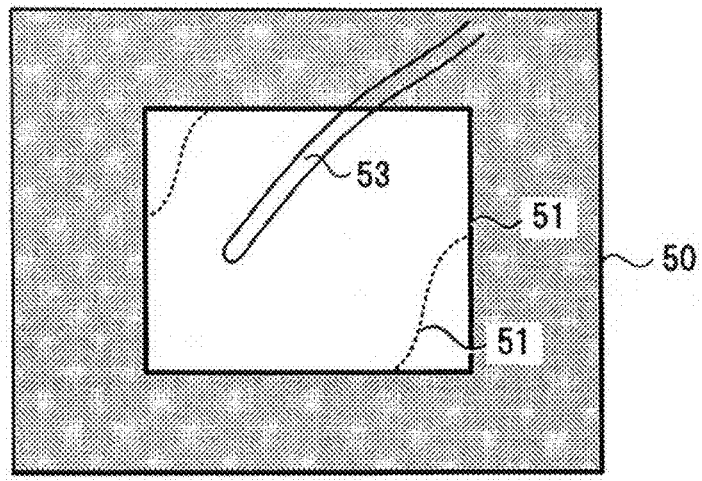
FIGS. 13A to 13C are explanatory diagrams showing a ROI changing process according to a third embodiment.
Figure 13B:
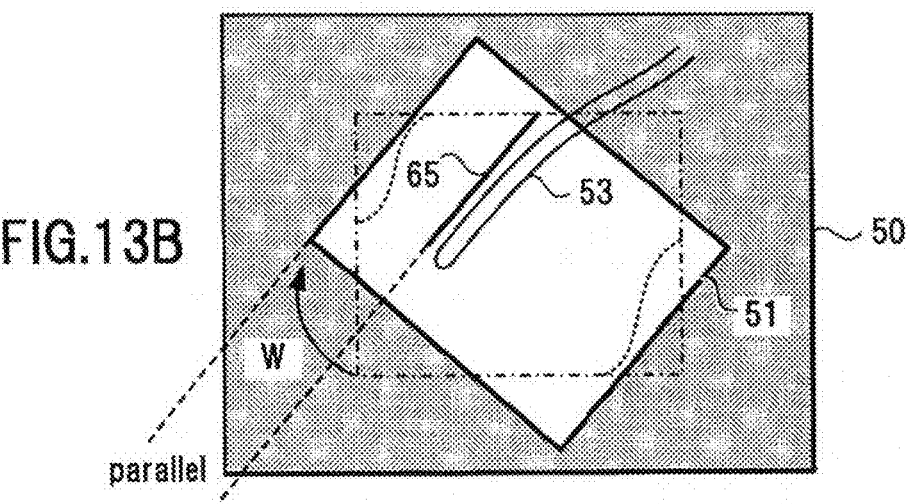
Figure 13C:
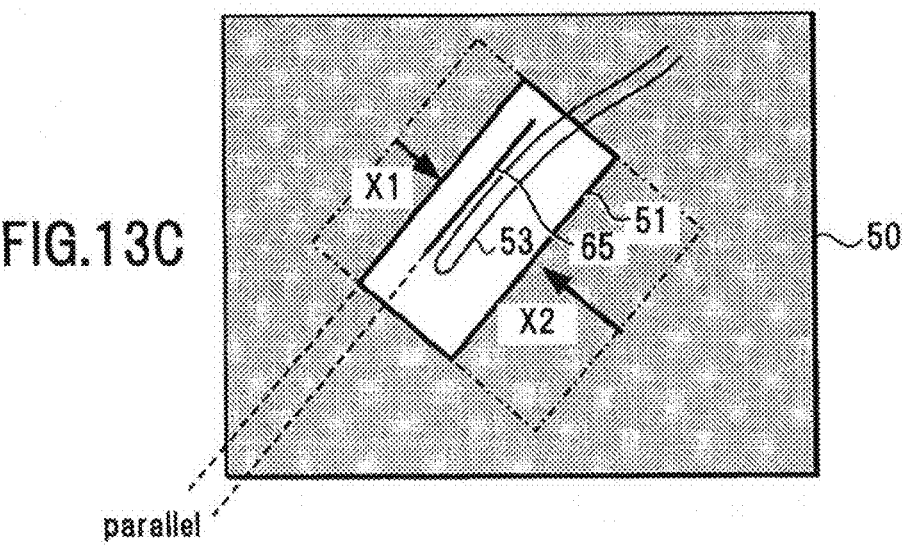

FIGS. 13A to 13C are diagrams illustrating a ROI changing process according to the third embodiment.

As shown in FIG. 13A, on the ROI fluoroscopic image 51, which is obtained as the irradiation field is narrowed by the collimator blades 121A and 121B, the device image 53 is displayed. Then, as shown in FIG. 13B, a user operates the mouse 342 to draw a straight line 65 near the device image 53 in such a way that the straight line 65 runs substantially parallel to a longitudinal direction of a mouse image 63. The image processing unit 32 determines which portion of the ROI fluoroscopic image 51 the straight line 65 is drawn in. When the straight line 65 is drawn, the ROI is rotated in such a way that one side of the ROI becomes parallel to the drawn straight line 65. The image processing unit 32 transmits information about the rotated ROI to the collimator mechanism control unit 41 via the system control unit 33.

As shown in FIG. 13C, the collimator mechanism control unit 41 rotates the rotation unit 122 of the X-ray beam limiting device 12 in the direction of 'W'. Moreover, in response to an operation by the user, the collimator mechanism control unit 41 controls the movements of the collimator blades 121A and 121B in such a way that the collimator blades 121A and 121B move closer to the device image 53, thereby changing the ROI. For example, the collimator blades 121A are moved in X1- and X2-directions. As a result, the ROI fluoroscopic image 51 is decreased in size, and the subject P's exposure to radiation is reduced.

Incidentally, the positions of the collimator blades 121A and 121B may be set in advance so as to approach a preset distance from the straight line 65. The ROI may be automatically changed with respect to the drawn straight line 65. Therefore, even when the device image 53 extends diagonally, the X-ray beam limiting device 12 is rotated in accordance with the inclination angle of the device image 53, and the positions of the collimator blades 121A and 121B are controlled. In this manner, the ROI can be changed.

Incidentally, as shown in FIG. 6A, if the ROI is away from the center of the FPD 21, and if an X-ray is emitted to outside the FPD 21 after the ROI is rotated, a warning message may be issued to urge a user to stop the rotation of the X-ray beam limiting device 12.

Figure 14:
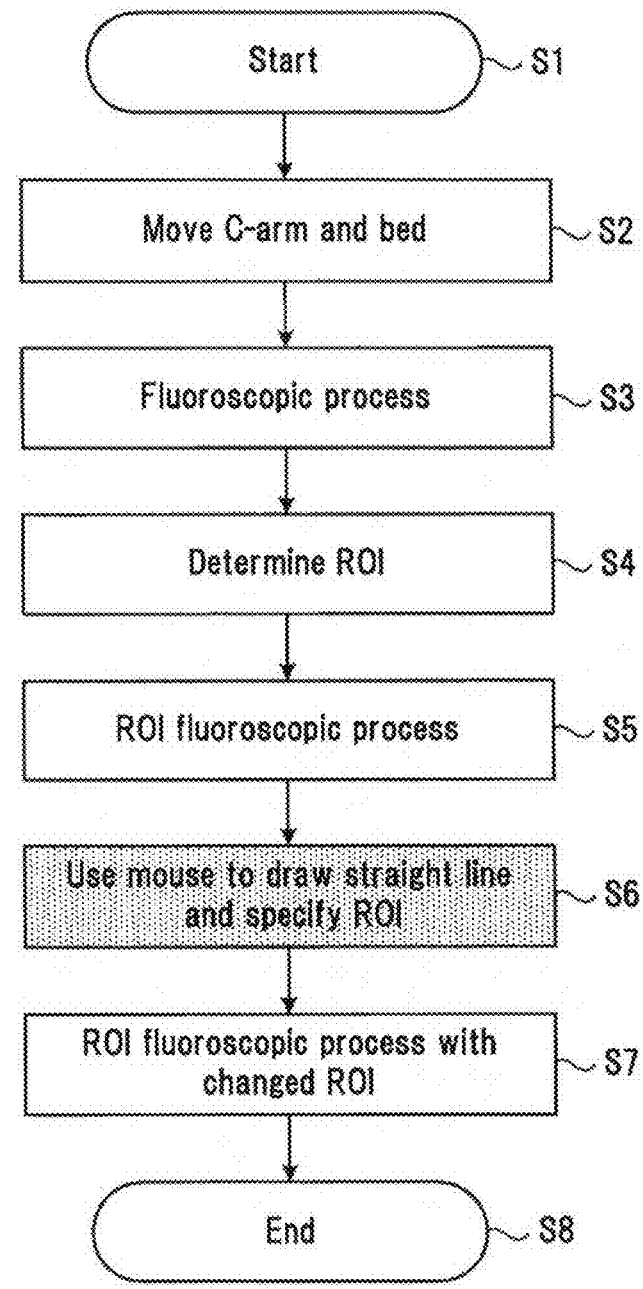
FIG. 14 is a workflow diagram showing a ROI changing process of the third embodiment from user's point of view.

FIG. 14 is a workflow diagram showing a ROI changing process of the third embodiment from user's point of view. In the case of FIG. 14, steps S1 to S5 are the same as those of the second embodiment. However, step S6 is different. That is, at step S6, as the mouse 342 of the operation unit 34 is operated, the straight line 65 is drawn near the device image 53, and the ROI is specified. At step 97, the changed ROI is used to carry out a ROI fluoroscopic process. Moreover, at step S7, the user moves the device forward while checking the position of the device, and the process comes to an end at step S8.

FIG. 15 is a workflow diagram showing a ROI changing process of the third embodiment from system's point of view. In the case of FIG. 15, steps S11 to S17 are the same as those of the second embodiment. However, step S18 is different.

That is, at step S18, the ROI is so rotated that the straight line 65 drawn by the user is parallel to one side of the ROI (see FIG. 13B). However, as described in FIG. 6, if the rotation angle is such that an X-ray is emitted to outside the FPD 21, a message is issued to ban the rotation.

At the next step S19, as the ROI is rotated, the collimator mechanism control unit 41 is notified of new ROI information. The collimator mechanism control unit 41 moves the collimator blades 121A and 121B to the notified position (see FIG. 13C). At step S20, the ROI fluoroscopic image 51, which is designed to see through with the changed ROI, is superimposed on the LIH image 52, and is displayed. The process comes to an end at step S21.

According to the above-described third embodiment, by drawing the line 65 that is substantially parallel to the device image within the ROI, the rotation angle of the ROI is specified. Moreover, the ROI is so changed as to exist in a preset region around the drawn line 65. Therefore, it is possible to reduce radiation exposure for the subject P.

In that manner, it is possible to assist the progression of the device, and reduce the subject's exposure to radiation.

While certain embodiments have been described, these embodiments have been presented by way of example only, and are not intended to limit the scope of the invention. Indeed, the novel apparatus and methods described herein may be embodied in a variety of other forms; furthermore, various omissions, substitutions and changes in the form of the apparatus and methods described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising:
an imaging unit that includes an X-ray tube which emits an X-ray to a subject, and an X-ray detector which detects an X-ray passing through the subject;

an X-ray beam limiting unit that is disposed between the X-ray tube and the X-ray detector, has a plurality of collimator blades, and can be rotated;

an image processing unit that detects a target based on an image data of a fluoroscopic image of a region of interest set by the X-ray beam limiting unit, and calculates components of a line of the target within the region of interest; and a control unit that individually controls the plurality of collimator blades in such a way that a long side of an opening formed by the plurality of collimator blades goes in a longitudinal direction of the calculated components of the line within the fluoroscopic image.

2. The X-ray diagnosis apparatus according to claim 1, wherein:

the image processing unit generates a fluoroscopic image of a situation where a device is being inserted into the subject; and the control unit regards an image of the device contained in the fluoroscopic image as the target, and controls rotation and movement of the plurality of collimator blades.

3. The X-ray diagnosis apparatus according to claim 2, wherein:

the image processing unit detects the device contained in a fluoroscopic image of the region of interest; and the control unit controls rotation of the X-ray beam limiting unit in such a way that a long side of an opening formed by the plurality of collimator blades goes in a direction in which the device extends.

4. The X-ray diagnosis apparatus according to claim 2, wherein the control unit rotates the X-ray beam limiting unit, and moves at least one of the collimator blades in such a way that the collimator blade approaches a preset distance from the target.

5. The X-ray diagnosis apparatus according to claim 1, wherein the image processing unit uses a fluoroscopic LIH (Last Image Hold) image as a background image, and superimposes on the LIH image, a fluoroscopic image that is obtained as an irradiation field is narrowed by the X-ray beam limiting unit.

6. An X-ray diagnosis assisting method comprising:

including an imaging unit that includes an X-ray tube which emits an X-ray to a subject, and an X-ray detector which detects an X-ray passing through the subject;

placing, between the X-ray tube and the X-ray detector, an X-ray beam limiting unit that has a plurality of collimator blades and can be rotated;

generating a fluoroscopic image of a region of interest set by the X-ray beam limiting unit;

detecting a target of the fluoroscopic image based on an image data of the region of interest;

calculating components of a line of the target within the region of interest; and controlling individually the plurality of collimator blades in such a way that a long side of an opening formed by the plurality of collimator blades goes in a longitudinal direction of the components of the line within the fluoroscopic image.

7. The X-ray diagnosis assisting method according to claim 6, wherein:

generating a fluoroscopic image of a situation where a device is being inserted into the subject; and controlling a rotation and movement of the plurality of collimator blades, an image of the device contained in the fluoroscopic image is regarded as the target.

8. The X-ray diagnosis assisting method according to claim 7, wherein:

detecting the device contained in a fluoroscopic image of the region of interest; and rotating the X-ray beam limiting unit in such a way that a long side of an opening formed by the plurality of collimator blades goes in a direction in which the device extends.

9. The X-ray diagnosis apparatus according to claim 1, wherein the image processing unit obtains coordinates of a start point and an end point of the target within the region of interest, and calculates a straight line connecting the start point and the end point as the components of the line.

10. The X-ray diagnosis assisting method according to claim 6, further comprising:

obtaining coordinates of a start point and an end point of the target within the region of interest; and calculating a straight line connecting the start point and the end point as the components of the line.

* * * * *